United States Patent
Andrekson et al.

(10) Patent No.: US 10,536,218 B2
(45) Date of Patent: Jan. 14, 2020

(54) FREE-SPACE OPTICAL COMMUNICATION LINKS WITH IMPROVED SENSITIVITY

(71) Applicants: Peter Avo Andrekson, Gothenburg (SE); Samuel Lars Ivar Olsson, Matawan, NJ (US)

(72) Inventors: Peter Avo Andrekson, Gothenburg (SE); Samuel Lars Ivar Olsson, Matawan, NJ (US)

(*) Notice: Subject to any disclaimer, the term of this patent is extended or adjusted under 35 U.S.C. 154(b) by 0 days.

(21) Appl. No.: 15/540,289

(22) PCT Filed: Feb. 20, 2017

(86) PCT No.: PCT/US2017/018556
§ 371 (c)(1),
(2) Date: Jun. 28, 2017

(87) PCT Pub. No.: WO2018/057054
PCT Pub. Date: Mar. 29, 2018

(65) Prior Publication Data
US 2019/0207679 A1 Jul. 4, 2019

Related U.S. Application Data

(60) Provisional application No. 62/398,700, filed on Sep. 23, 2016.

(51) Int. Cl.
*H04B 10/112* (2013.01)
*H04B 10/297* (2013.01)
(Continued)

(52) U.S. Cl.
CPC ....... *H04B 10/1125* (2013.01); *H04B 10/112* (2013.01); *H04B 10/2971* (2013.01);
(Continued)

(58) Field of Classification Search
CPC ............ H04B 10/1125; H04B 10/2971; H04B 10/504; H04B 10/18; H04B 10/556;
(Continued)

(56) References Cited

U.S. PATENT DOCUMENTS 5,596,667 A * 1/1997 Watanabe ............. G02F 1/3538
372/21
5,798,853 A * 8/1998 Watanabe .......... H04B 10/2531
359/300

(Continued)

FOREIGN PATENT DOCUMENTS

EP    2 346 122 A2    7/2011

OTHER PUBLICATIONS

Slavik, Radan, et al., "All-Optical Phase and Amplitude Regenerator for Next-Generation Telecommunications systems".
(Continued)

*Primary Examiner* — Abbas H Alagheband
(74) *Attorney, Agent, or Firm* — Wendy W. Koba

(57) ABSTRACT

A free-space optical communication link is proposed that utilizes phase-sensitive amplification of the received optical signal at the input to the receiver portion of the link. The transmitter component of the FSO link generates an idler signal that is transmitted through free space with the original data signal and used at the PSA in conjunction with a pump wave to impart gain onto the received information signal. The PSA performs four-wave mixing (FWM) of the data, idler and pump to create the amplified data signal. In one embodiment, the pump wave used to generate the idler at the transmitter is sent through free space with the information and idler signals and used by the PSA to perform amplification. Alternatively, the PSA may use a co-located pump laser, in combination with the received idler signal, to perform the phase-sensitive amplification process.

21 Claims, 2 Drawing Sheets

(51) Int. Cl.
  *H04B 10/50* (2013.01)
  *H01S 3/067* (2006.01)
  *H04B 10/293* (2013.01)
  *H03F 3/08* (2006.01)
  *G01N 21/17* (2006.01)

(52) U.S. Cl.
  CPC .......... *H04B 10/504* (2013.01); *G01N 21/17* (2013.01); *H01S 3/067* (2013.01); *H03F 3/08* (2013.01); *H04B 10/293* (2013.01)

(58) Field of Classification Search
  CPC .... H04B 10/297; H04B 10/50; H04B 10/112; H04B 10/70; G01N 21/17; G01N 21/00; G02B 6/24; G02B 6/26; G02B 6/00; G02F 1/35; G02F 1/39; G02F 2/02; H01S 3/067; H01S 3/005; H01S 3/0078; H01S 3/1608; H01S 3/06754; H01S 3/10; H04L 9/0852; H01L 29/02; H01L 29/06; G06N 10/00; B82Y 10/00
  USPC ....................................................... 398/129
  See application file for complete search history.

(56) References Cited

U.S. PATENT DOCUMENTS

| | | | | |
|---|---|---|---|---|
| 6,304,348 | B1* | 10/2001 | Watanabe | H04B 10/2531 398/9 |
| 6,501,591 | B1* | 12/2002 | Kumar | G02F 1/395 359/326 |
| 6,897,434 | B1* | 5/2005 | Kumar | B82Y 10/00 250/227.18 |
| 7,164,526 | B2* | 1/2007 | McKinstrie | G02F 1/395 330/4.5 |
| 7,630,126 | B2* | 12/2009 | McKinstrie | G02F 1/395 330/4.5 |
| 7,724,421 | B2 | 5/2010 | McKinstrie | |
| 8,774,635 | B2 | 7/2014 | Juarez et al. | |
| 8,837,948 | B2 | 9/2014 | Carlson et al. | |
| 8,912,475 | B2 | 12/2014 | Smith et al. | |
| 8,922,874 | B2 | 12/2014 | Inafune et al. | |
| 9,002,151 | B2* | 4/2015 | Woodward | G01J 1/42 385/12 |
| 9,065,243 | B2 | 6/2015 | Asobe et al. | |
| 9,246,624 | B1 | 1/2016 | Yang et al. | |
| 9,377,668 | B2 | 6/2016 | Brun et al. | |
| 9,413,456 | B2 | 8/2016 | Hunt et al. | |
| 2002/0048079 | A1* | 4/2002 | Popov | H01S 3/1083 359/333 |
| 2006/0045445 | A1* | 3/2006 | Watanabe | G02F 1/3515 385/122 |
| 2008/0158656 | A1* | 7/2008 | McKinstrie | G02F 1/3536 359/330 |
| 2010/0147674 | A1* | 6/2010 | Krivoshlykov | G02B 6/122 204/157.4 |
| 2012/0315049 | A1* | 12/2012 | Banwell | H04B 10/25759 398/115 |
| 2013/0071113 | A1* | 3/2013 | McKinstrie | H04B 10/25 398/39 |
| 2013/0089888 | A1* | 4/2013 | Woodward | G01J 1/42 435/34 |
| 2013/0126701 | A1* | 5/2013 | Smith | H03F 3/08 250/206 |
| 2013/0128341 | A1 | 5/2013 | Ellis et al. | |
| 2013/0208334 | A1* | 8/2013 | Kakande | H04B 10/291 359/246 |
| 2014/0198375 | A1* | 7/2014 | Yang | H04B 10/50 359/330 |
| 2015/0036210 | A1* | 2/2015 | Asobe | G02F 1/39 359/341.3 |
| 2016/0357088 | A1* | 12/2016 | McKinstrie | G02F 1/39 |
| 2017/0272171 | A1* | 9/2017 | Almaiman | H04B 10/2507 |
| 2018/0097567 | A1* | 4/2018 | LeGrange | H04B 10/118 |

OTHER PUBLICATIONS

Okamura, Yasuhiro, et al., "Frequency Nondegenerate Optical Parametric Phase-Sensitive Amplifier Repeater by Using Recovered Pump Carrier Generated from Phase-Conjugated Twin Waves", Optical Society of America, OFC 201.

Marhic, Michel E., et al., "Fiber Optical Parametric Amplifiers in Optical Communication Systems", Laser Photonics, Rev. 9, No. 1, 2015, pp. 50-74.

* cited by examiner

FREE-SPACE OPTICAL COMMUNICATION LINKS WITH IMPROVED SENSITIVITY

CROSS-REFERENCE TO RELATED APPLICATIONS

This application claims the benefit of U.S. Provisional Application Ser. No. 62/398,700, filed Sep. 23, 2016 and herein incorporated by reference.

TECHNICAL FIELD

The present invention relates to a free-space optical communication system and, more particularly, to the utilization of phase-sensitive amplification as a pre-amplifier at the input to the optical receiver to improve the overall performance of the free-space link.

BACKGROUND OF THE INVENTION

Free-space optical communication links are increasingly being used for relatively short links (e.g., about 1 km), which are often established for temporary purposes (e.g., sporting event, outdoor concert venue, and the like). By their nature, these links provide the advantages of high capacity and low latency. Free-space links are similarly being explored for extremely long links (e.g., out of the earth's orbit, between satellites, etc.). In either case of "relatively short" or "extremely long" links, the sensitivity of the link is fundamentally limited by the effects of diffraction (i.e., the continual divergence of a free-space optical beam as it travels from a transmitter to a receiver). In this context, sensitivity is defined as the signal strength required to recover the transmitted information with sufficient fidelity. As there are practical limits on the size of the apertures permitted at both the transmitter and receiver, the effects of diffraction result in only a portion of the diverging beam being captured at the receiver (as a function of the aperture size/optical components at the receiver).

While improving the receiving optics allows for a larger portion of the signal to be captured, the expense associated with this approach is not always suitable for a given application. Another approach to improving the sensitivity of a free space optical receiver is to utilize advanced modulation schemes at the transmitter which allow for the data to be transmitted at lower power, or the like.

It is apparent that an alternative approach to providing a free space optic link that remains within the power budget allotted for practical applications is required.

SUMMARY OF THE INVENTION

The needs remaining in the prior art are addressed by the present invention, which relates to a free-space optical communication system and, more particularly, to the utilization of a phase-sensitive amplifier (PSA) as a pre-amplifier at the input to the receiver portion of a free-space optic (FSO) link.

In accordance with one or more embodiments of the present invention, a transmitter component of the FSO communication link is configured to generate an idler signal that is transmitted through free space along with the original information signal and used at a PSA disposed as a pre-amplifier at the input to the free-space optical receiver to impart amplitude gain (i.e., amplification) to the received information signal. The PSA includes a nonlinear optical element that performs phase-sensitive amplification, relying on a nonlinear four-wave mixing (FWM) process. In this process, energy is transferred from a pump wave to both the information signal and the idler signal, as dictated by the relative phases of the three components (i.e., the information signal, the idler signal and the pump wave) as they enter the nonlinear optical element.

In one embodiment, the pump wave used to generate the idler signal (in combination with the information signal) is transmitted through free space with the information signal and the idler signal, so as to be used by the PSA to perform amplification. Alternatively, the PSA may use a co-located pump laser, in combination with the received information and idler signals, to perform the phase-sensitive amplification process on the received information signal.

In accordance with one embodiment of the present invention, the idler signal is created by using a different wavelength, and sending a conjugated version of the information signal on the idler wavelength. Alternatively, in a polarization-controlled embodiment, the information signal may be transmitted along a first, defined polarization and the idler transmitted on the same wavelength, but along an orthogonal polarization direction. It is also possible to utilize a time-division system to transmit the information signal and its associated idler signal with a predetermined delay between the two, with the PSA at the receiver configured to incorporate a delay of similar length within the FWM system.

A specific embodiment of the present invention takes the form of an FSO link comprising a free-space optical transmitter including an idler generator, where the idler generator is responsive to an information signal and a pump wave for creating an idler signal as a conjugate of the information signal. Thereafter, the optical transmitter launches the information signal and the idler signal into free space. The FSO link also includes a free-space optical receiver positioned to receive a portion of the signals launched by the free-space optical transmitter and a phase-sensitive amplifier disposed at the input to the free-space optical receiver. The phase-sensitive amplifier includes a nonlinear optical element for performing four-wave mixing of the received information signal and the received idler signal with a pump wave to create as an output an amplified version of the received information signal. The amplified version of the received information signal is thereafter applied as an input to the free-space optical receiver.

Another embodiment of the present invention defines a method of providing free space optical communication comprising the steps of: providing an original information signal to be transmitted; supplying a pump wave; generating an idler signal from a combination of the information signal and the pump wave, the idler signal being a conjugate representation of the information signal; transmitting the information signal and the idler signal across a free space optical link to an optical receiver; performing phase-sensitive amplification on the received information signal, using the received idler signal and an associated pump wave; and providing the amplified information signal produced by phase-sensitive amplification as an input to an optical receiver.

Other and further embodiments and attributes of the present invention will become apparent during the course of the following discussion and by reference to the accompanying drawings.

BRIEF DESCRIPTION OF THE DRAWINGS

Referring now to the drawings.

DETAILED DESCRIPTION

One of the essential aspects that dictates the capacity and reach of any FSO link is the system power budget. This, in turn, depends on several metrics including, but not limited to, the launch power available at the transmitter and the sensitivity of the receiver (the latter determined as a function of the given data information bit rate and modulation format). The resulting power budget thus determines the maximum allowable loss in the transmission link—and thus also in practice the reach of the link (i.e., the distance between the transmitter and receiver).

It is proposed in accordance with the present invention to utilize a PSA in conjunction with an optical receiver in an FSO link to improve the sensitivity of the receiver. By virtue of using a PSA at the receiver input, additional margin in the overall power budget of the FSO link is provided. Inasmuch as an FSO link does not experience the types of dispersions and nonlinearities associated with fiber-based systems, it is contemplated that the specific design and configuration of the PSA itself is less complicated than known PSAs used in association with fiber-based communication systems (which need to account for fiber dispersion, nonlinearities, and the like).

Importantly, the inventive PSA-based approach for improving receiver sensitivity can be combined with virtually any modulation scheme for transmitting optical signals, as well as with high efficiency optics within the receiver. Thus, in some sense, the inventive PSA-based approach may be a significant "add-on" feature to existing solutions for increasing receiver sensitivity in an FSO link. The increased sensitivity offered by the PSA approach may also be traded for lower launch power and/or smaller (less expensive) aperture optics and/or higher capacity throughput or extended reach.

Figure 1:
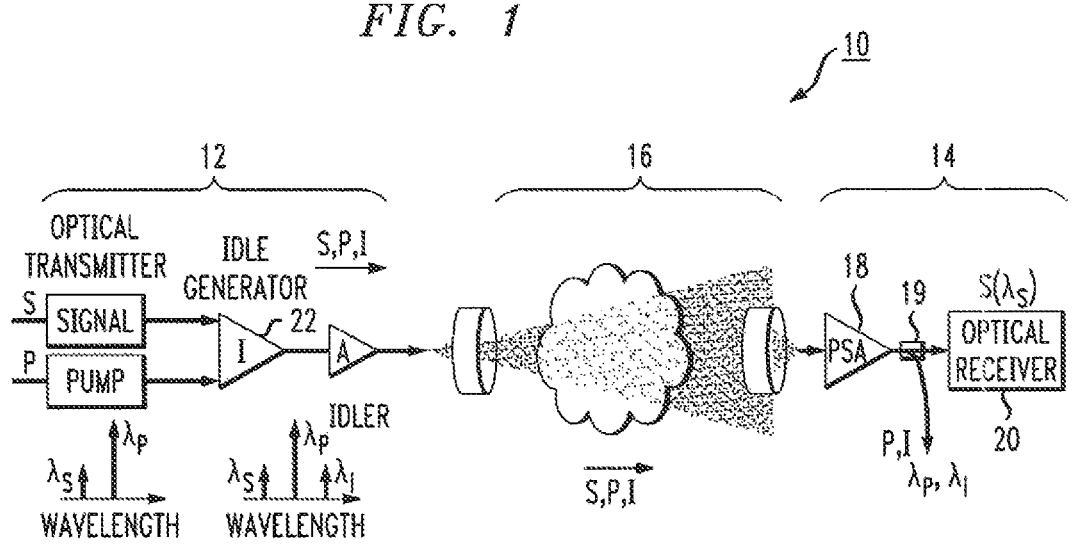
FIG. 1 is a simplified diagram of an exemplary free-space optical communication system formed in accordance with the present invention, illustrating the inclusion of a PSA at the input to the receiver component.

FIG. 1 illustrates an exemplary FSO communication link 10 formed in accordance with one embodiment of the present invention. As shown, FSO communication link 10 includes a free-space optical transmitter 12 for communicating a given optical information signal S (which may be presented in any suitable modulation format). Transmitter 12 is utilized to provide a pump wave P and generate an idler signal I (based on a combination of information signal S and pump wave P) that is communicated through free space with the information signal S toward a free-space optical receiver 14. The transmission of S, P and I is shown as occurring across a free-space link 16, where as discussed above the three separate optical beams will experience divergence as they propagate through free space toward receiver 14. One characteristic of an FSO link is defined as the "reach", that is the maximum distance that receiver 14 may be separated from transmitter 12 and still capture a sufficient portion of the divergent beam to enable an accurate recovery of the transmitted information. As will be discussed in detail below, the inclusion of a PSA at the input of receiver 14 enables for the reach to be increased over prior art configurations.

In accordance with this embodiment of the present invention, free space optical receiver 14 includes a PSA 18 that utilizes the received pump wave P and idler signal I to provide amplification of the received information signal S. As will be described in detail below, PSA 18 performs four-wave mixing of the three wavelengths associated with the signal, idler and pump, using the conjugate information present in the idler signal and the relative phase information between the three waves to create an amplified version of the received information signal. Once the amplification is performed, the pump and idler may be removed from the optical path (using, for example, an optical filter component 19), providing the amplified information signal as an input to a conventional optical receiver module 20.

Utilized as a pre-amplifier at the receiver, PSA 18 provides the best possible receiver sensitivity, since it has a quantum-limited noise figure of 0 dB. That is, the position of PSA 18 at the input of receiver 20 does not impact or degrade the signal-to-noise ratio (SNR) of the signal in the process of amplifying the received light. This is in contrast to all other optical amplifiers (including conventional fiber-based amplifiers), which have a minimum quantum-limited noise figure of 3 dB.

The added sensitivity associated with using PSA 18 at the front-end of receiver 20 has a variety of advantages. For example, it can enhance (extend) the reach of FSO link 10, it can reduce the size of the associated optics (aperture size) necessary at the transmitter and/or receiver, it can reduce the required launch power and, finally, it can increase the link capacity.

In this specific embodiment as shown in FIG. 1, PSA 18 is shown as a two-mode PSA, which utilizes three different light waves (pump, information, and idler) to perform four-wave mixing in a manner that generates an amplified information signal S with minimal noise. Accordingly, free-space optical transmitter 12 is specifically configured to generate an idler signal that co-propagates through free space with the information signal and the pump wave. Transmitter 12 is shown as including an idler generator 22 that receives as inputs the optical information signal (operating at wavelength $\lambda_s$) and a pump wave (supplied by a CW pump laser, operating at a known wavelength $\lambda_p$). As discussed below, idler generator 22 includes a nonlinear optical component that performs four-wave mixing of the information signal and the pump to generate an idler signal at wavelength $\lambda_i$. The idler signal is a conjugate copy of the information signal, and propagates at a wavelength which is double the wavelength of the pump less the signal wavelength (i.e., $\lambda_i = 2\lambda_p - \lambda_s$). An optical amplifier 24 (which may comprise a fiber-based amplifier, for example a distributed Raman amplifier (DRA) or an erbium-doped fiber amplifier (EDFA), etc.) may be disposed within transmitter 12 at the output of idler generator 22 and used to boost the power of all three waves prior to launching the beams into free space. At times, a power boost to the order of about 1 W has been found necessary to provide the desired reach for a given FSO communication link. It is to be understood that optical amplifier 24 is an optional component in the inventive FSO communication link.

Figure 2:
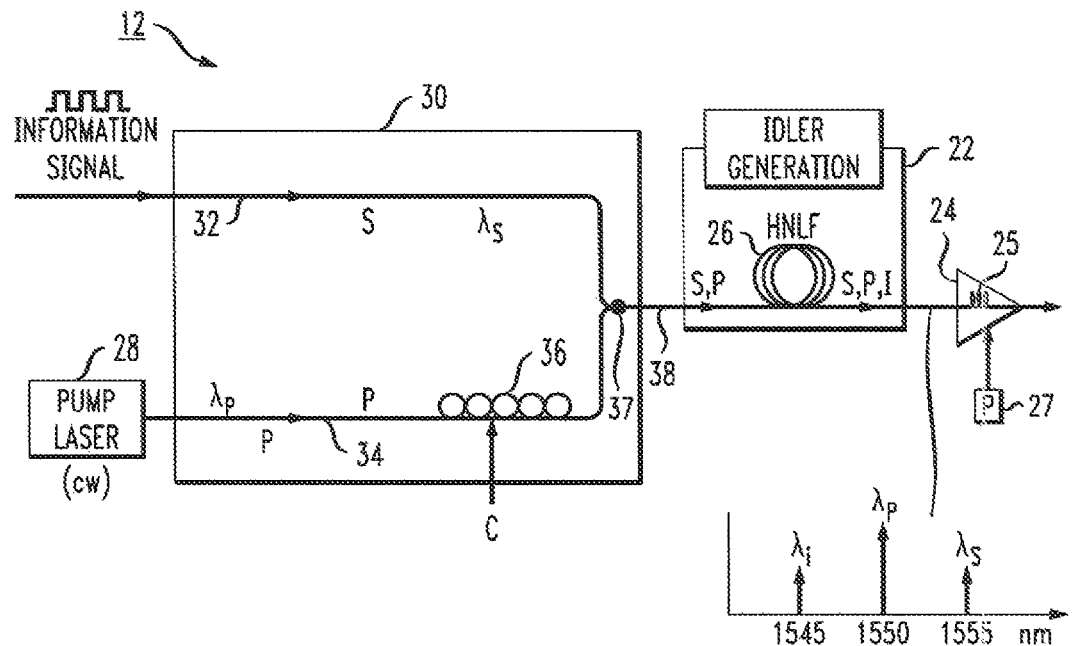
FIG. 2 illustrates an exemplary free-space optical transmitter that may be utilized within the link shown in FIG. 1.

FIG. 2 illustrates a specific configuration of an exemplary free-space optical transmitter 12 formed in accordance with the present invention for use with the specific arrangement shown in FIG. 1. Also shown in FIG. 2 is a pump laser 28 used to provide the pump wave at the desired wavelength $\lambda_p$. Transmitter 12 of FIG. 2 is shown as further comprising an optical coupler module 30 used to inject both the pump wave P and information signal S onto the same signal path at the input to idler generator 22. As shown, module 30 includes a first signal path 32 (such as an optical fiber, or waveguide integrated within an optical medium) for supporting the propagation of the information signal S. A second signal path 34 is coupled to pump 28 and used to support the propagation of the CW pump wave P. A polarization controller 36 may be included along second signal path 34 and used to adjust (via an external control signal C) the polarization state of the pump wave so that the parametric gain within idler generator 22 is maximized. It is to be understood that the inclusion of polarization controller 36 is optional.

First and second optical signal paths 32 and 34 are shown as applied as inputs to a wavelength division multiplexer (WDM) 37 (or any other suitable type of optical coupler), which is used to combine information signal S (operating at wavelength $\lambda_s$) and the pump wave P (operating at wavelength $\lambda_p$) onto a single output signal path, shown as optical fiber 38 in FIG. 2. Thereafter, optical fiber 38 is used as the input to idler generator 22, which functions in the manner described above to generate the idler signal as a conjugate of the information signal, propagating on a wavelength derived from a combination of the pump and signal wavelengths. In this embodiment, idler generator 22 is shown as comprising a section of highly-nonlinear optical fiber (HNLF) 26 which is known to be able to perform four-wave mixing (FWM) on optical waves propagating along the extent of the fiber. In accordance with the principles of four-wave mixing, the separation $\Delta\lambda$ between $\lambda_s$ and $\lambda_p$ is a factor in generating a suitable idler signal. In one embodiment, a $\Delta\lambda$ on the order of 5 nm was found sufficient for use with an information signal operating at a wavelength $\lambda_s$ of 1555 nm; that is, a pump wave operating at a wavelength $\lambda_p$ of 1550 nm is a suitable candidate. The mixing of these two waves results in the creation of an idler signal I (carrying a conjugate form of the data appearing within information signal S), propagating at a wavelength $\lambda_I$ of 1545 nm.

As mentioned above, optical amplifier 24 may be included in transmitter 12 to boost the power of all three waves (S, I, and P) launched into free space. FIG. 2 illustrates an exemplary EDFA component 24 disposed at the output of idler generator 22. In this case, component 24 comprises a section of erbium-doped optical fiber 25, with an external pump source 27 (operating at, for example 980 nm) providing amplification to all three waves passing through amplifier 24. At times, an increase to a power level the order of about 1 W has been found necessary to provide an FSO link of acceptable performance.

It is to be understood that HNLF 26 is only one exemplary nonlinear component that may be used to create the idler signal from the original information signal and pump. Alternative bulk optic materials, waveguide structures or optical nanowires that impart a known degree of nonlinearity to propagating optical signals may be used. These various nonlinear components may comprise silicon, SiN, GaAs, or the like. Other types of nonlinear systems may also be developed for use. In yet a different configuration, an arrangement such as an optical comb generator may be used to create the "triplet" of signal, pump, and idler, with each using a separate wavelength generated by the comb. In embodiments where an optical comb is used, the idler signal still needs to be a conjugate representation of the information signal.

As mentioned above, one advantage of using the PSA pre-amplifier system of the present invention is that it may be used with other techniques for improving the overall performance of an FSO communication link. For example, the transmitter portion of the FSO link may be configured to transmit the information signal using advanced modulation techniques (known to also improve receiver sensitivity). In this case, the idler signal generated within element 22 will need to be a conjugate form of this version of the data signal.

While all three of these beams will experience divergence as they propagate from transmitter 12 to receiver 14, all will continue to propagate at their given wavelength, and not experience the type of wavelength-shift (dispersion) common in fiber-based systems. Advantageously, therefore, PSA 18 is able to provide parametric amplification of the received information signal with a noise figure approaching 0 dB. In particular, PSA 18 includes a nonlinear optical element that performs phase-sensitive amplification, relying on a nonlinear four-wave mixing (FWM) process. In this process, energy is transferred from the pump wave to both the information signal and the idler signal, as dictated by the relative phases of the three components (the information signal, the idler signal, and the pump wave) upon entering the nonlinear optical element.

Figure 3:
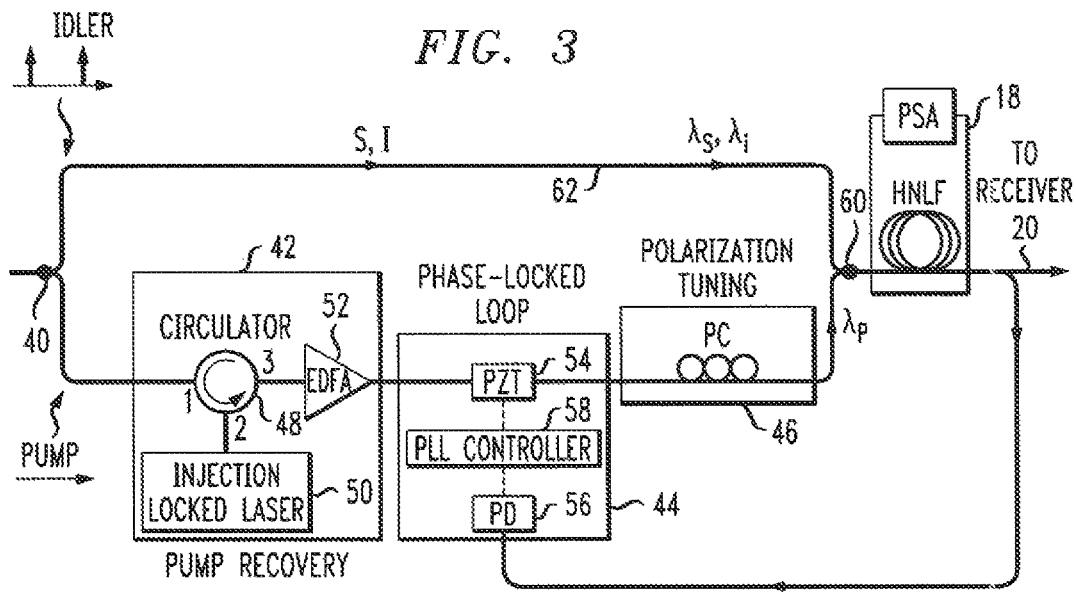
FIG. 3 illustrates an exemplary pump recovery path that may be used at the input to the PSA in accordance with the present invention.

FIG. 3 illustrates in more detail an exemplary pump path that may be utilized with PSA 18 to improve the characteristics of the received pump wave in a manner that improves the results of the four-way mixing process within PSA 18. In this embodiment, an input WDM 40 is used to separate the received pump wave from the received information and idler signals, and performs restoration on the pump wave in order to improve the operation of PSA 18. Referring to FIG. 3, the pump path is shown to include a pump recovery module 42, a phase-locked loop 44 and, optionally, a polarization tuning component 46. The incoming pump wave, as separated out by WDM 40, is applied as an input to pump recovery module 42. As shown, the pump wave is applied as an input to a first input port of an optical circulator 48. An injection-locked laser 50 (i.e., a "local" pump laser operating at the same pump wavelength $\lambda_p$ and located at the receiver) is coupled to a second input port of circulator 48. Local laser 50 functions to "lock" in both phase and frequency to the incoming pump wave, effectively regenerating the pump wave. The regenerated pump wave then exits circulator 48 at its output port. Optionally, a fiber-based amplifier 52 (such as an erbium-doped fiber amplifier, EDFA) may be included at the output of circulator 48 and used to boost the power of the regenerated pump wave.

Continuing with the description of the pump signal path, the regenerated (and perhaps amplified) pump wave is then applied as an input to PLL component 44. As shown, the pump wave passes through a piezo-electric transducer (PZT) element 54. As also shown, a portion of the amplified information output signal from PSA 18 is fed back and used as input to PLL component 44. Here, the feedback signal is detected by a photodetector 56, with the electrical output from photodetector 56 applied as an input to a PLL controller 58. PLL controller 58 itself generates a high voltage DC signal that is fed to PZT element 54. The application of this DC voltage to PZT element 54 functions to change its "optical length" such that the pump wave is properly phasematched with the received information and idler signals applied as inputs to PSA 18. The error-corrected pump signal thereafter passes through (optional) polarization controller 46, which functions to adjust the polarization of the pump, relative to the polarization of the signal and idler such that maximum PSA gain is achieved. In this particular embodiment as shown in FIG. 3, a WDM element 60 is used to couple the "regenerated" pump output from polarization controller 46 with the idler and information signals (propagating along a separate waveguide (fiber) 62), combining the regenerated pump, idler and signal to be applied as inputs to PSA 18. PSA 18 then functions in the manner described above to provide parametric amplification of the received information signal, based on four-wave mixing of the information, idler, and regenerated pump.

Figure 4:
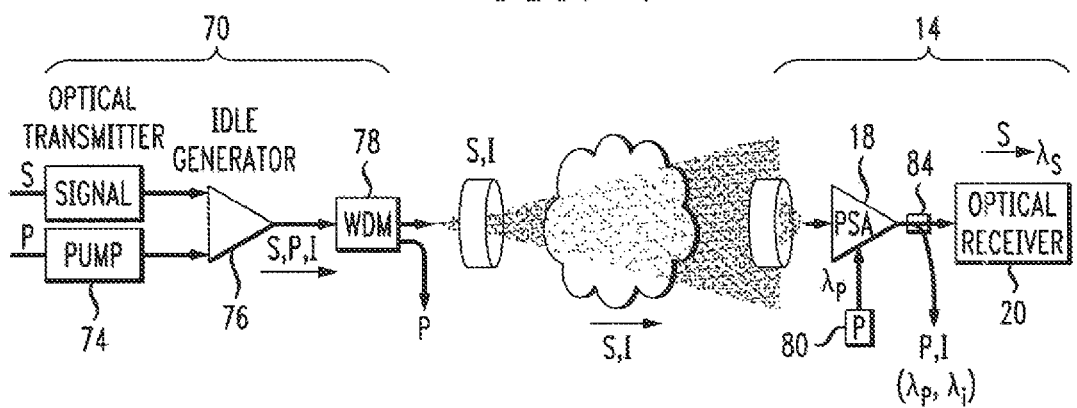
FIG. 4 illustrates an alternative embodiment of the present invention, using a pump co-located with the PSA and transmitting only the information and idler signals through free space between the transmitter and the receiver.

As mentioned above, there may be situations where it is not desirable to transmit the pump wave with the information and idler signals. Yet, a pump wave is required at PSA 18 in order to perform parametric amplification. FIG. 4 illustrates an alternative FSO communication link formed in accordance with this alternative embodiment of the present invention. As shown, only information signal S and associated idler signal I are transmitted across the free-space link between a free-space optical transmitter 70 and a free-space optical receiver 72. Similar to the embodiment described above, free-space optical transmitter 70 includes a pump laser 74, which is applied as a first input to an idler generator 76. The information signal S is applied as a second input to idler generator 76. As described in detail above, idler generator 76 utilizes a nonlinear optical element (or, perhaps, an optical comb) to create an idler signal I that carries the conjugate form of the data within information signal S, at a wavelength $\lambda_i$ based upon the combination of $\lambda_s$ and $\lambda_p$.

In accordance with this alternative embodiment of the present invention, the pump wave used to create the idler signal is removed from the optical path prior to launching the beams into free space. Referring to FIG. 4, transmitter 70 is shown as including a WDM 78 (or similar component) that is used to remove pump wave P (operating at $\lambda_p$), permitting only the beams propagating at $\lambda_s$ and $\lambda_i$ (that is, information signal S and associated idler signal I) to be launched by transmitter 70 into free space. While not shown in this illustration, it is to be understood that an optical amplifier may be disposed at the output of WDM 78 and used to increase the power of the information and idler signals prior to being launched. Therefore, in accordance with this embodiment of the present invention, elimination of the pump from the launched beams relaxes the power budget of the FSO link. That is, since one component of the power budget is the required power at the transmitter, the need to only launch two beams—the signal and the idler—reduces the power required at the input side.

Figure 5:
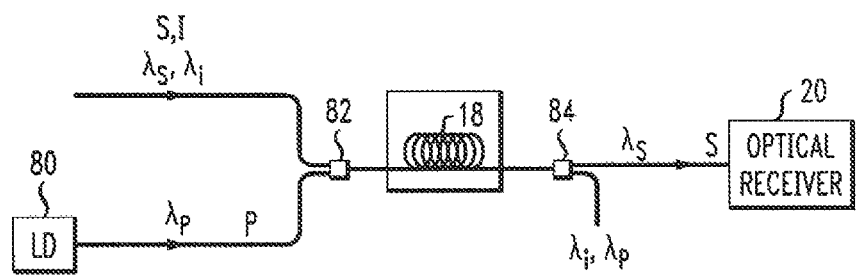
FIG. 5 contains a diagram illustrating an exemplary configuration for coupling the received information signal and idler signal with a locally-generated pump at the input of the PSA component.

Inasmuch as only the information signal S and idler signal I are received by free space optical receiver 72, it is necessary for a local pump laser to be included at the receiver in order to provide phase-sensitive amplification of the received information signal S in accordance with the principles of the present invention. Referring to FIGS. 4 and 5, a local pump laser 80 is included with PSA 18 and used to provide a pump wave (at the same $\lambda_p$ as used to create the idler signal at transmitter 70) with a known phase relation between the received information and idler signals. The locally-generated pump wave, information signal and idler signal are subsequently combined within a WDM 82 and thereafter applied as inputs to PSA 18 (which may comprise a section of HNLF, as used above). A four-wave mixing process as described above results in creating an amplified information signal. As before, once the information signal has been amplified, the idler signal and pump wave may be removed by filtering (as shown by WDM 84 in FIG. 5), with the amplified version of the information signal then applied as the signal input to optical receiver 20 for further processing.

The above-described exemplary embodiments of the present invention utilize wavelength diversity in the creation of the idler. It is to be understood that a free-space optical communication link formed in accordance with the present invention may be alternatively configured to utilize an idler propagating at the same wavelength as the information signal, but formed to propagate along an orthogonal polarization state with respect to a known, controlled polarization state of the information signal). In this polarization diversity embodiment, therefore, information signal S is necessarily provided along a polarization-maintaining fiber (or other type of PM waveguide). Alternatively, a time-slot diversity configuration may be used to create an idler signal that allows for phase-sensitive amplification to be performed at the input to the free-space optical receiver.

An advantage of the phase-sensitive amplification technique of the present invention is that it is able to work with any type of modulation scheme used to create the original information signal in the first instance. As mentioned above, various prior art FSO communication arrangements have utilized advanced modulation techniques (e.g., m-PPM) to improve receiver sensitivity. The phase-sensitive amplification technique of the present invention is able to provide gain to the information signals based on these advanced modulation techniques, as long as an appropriate idler signal (as a conjugate) is also created and sent with the information signal between the transmitter and the receiver. Other sensitivity improvement techniques, such as transmitting multiple copies of the same data at different wavelengths, spatial diversity techniques for transmitting copies of the data, etc. are all acceptable features that may be used in conjunction with the phase-sensitive amplification performed in accordance with the present invention.

Moreover, while it is contemplated that a "two-mode" PSA embodiment of the present invention is a preferred configuration (i.e., using the three waves described above: signal, idler, and pump), it is to be understood that the principles of the present invention can be extended to a "multi-mode" PSA arrangement. In particular, a "multi-mode" PSA configuration involves the use of additional pump waves and idler signals, further improving the receiver sensitivity. However, this increase in receiver sensitivity is achieved at the expense of spectral efficiency and the need to launch more power at the transmitter.

Indeed, while specific examples of the invention are described in detail above to facilitate explanation of various aspects of the invention, it should be understood that the intention is not to limit the invention to the specifics of the examples. Rather, the intention is to cover all modifications, embodiments and alternatives falling within the spirit and scope of the invention as defined by the appended claims.

What is claimed is:

1. A free-space optical communication link comprising
   a free-space optical transmitter including an idler generator, responsive to an information signal for creating an idler signal as a conjugate of the information signal, the optical transmitter for launching the information signal and the idler signal into free space;
   a free-space optical receiver positioned to receive a portion of the signals launched by the free-space optical transmitter; and a phase-sensitive amplifier disposed at an input to the free-space optical receiver, the phase-sensitive amplifier including a nonlinear optical element for performing four-wave mixing of the received information signal and the received idler signal with a pump wave to create as an output an amplified version of the received information signal, the amplified version of the received information signal thereafter applied as an input to the free-space optical receiver.

2. The free-space optical communication link as defined in claim 1 wherein the free-space optical transmitter further comprises a pump laser for supplying the pump wave, the free-space optical transmitter configured to transmit the pump wave through free space with the information signal and the idler signal.

3. The free-space optical communication link as defined in claim 2 wherein the information signal propagates at a wavelength $\lambda_s$, the pump wave propagates at a wavelength $\lambda_p$, and the idler signal created by the idler generator propagates at a wavelength $\lambda_i$, where $\lambda_i=2\lambda_p-\lambda_s$.

4. The free-space optical communication link as defined in claim 2 wherein the free-space optical transmitter further comprises a polarization controller disposed in a path between the pump laser and the idler generator.

5. The free-space optical communication link as defined in claim 1 wherein the free-space optical transmitter further comprises an optical amplifier disposed at an output of the idler generator.

6. The free-space optical communication link as defined in claim 1 wherein the idler generator provides an idler signal output with a polarization orthogonal to the information signal.

7. The free-space optical communication link as defined in claim 1 wherein the idler generator provides an idler signal output spaced in time with respect to the information signal.

8. The free-space optical communication link as defined in claim 1 wherein the idler generator comprises a nonlinear optical element.

9. The free-space optical communication link as defined in claim 8 wherein the nonlinear optical element comprises a section of highly-nonlinear optical fiber.

10. The free-space optical communication link as defined in claim 8 wherein the nonlinear optical element is selected from the group consisting of: bulk optic material, optical waveguides, and optical nanowires.

11. The free-space optical communication link as defined in claim 1 wherein the free-space optical transmitter includes an optical frequency comb for generating the information signal and the idler signal.

12. The free-space optical communication link as defined in claim 1 wherein the phase-sensitive amplifier includes a local pump laser for providing the pump wave to be used by the phase-sensitive amplifier.

13. The free-space optical communication link as defined in claim 1 wherein the phase-sensitive amplifier further comprises a filtering element disposed at the output thereof for removing the remaining pump wave and idler signal prior to applying the amplified version of the information data signal as an input to the free-space optical receiver.

14. The free-space optical communication link as defined in claim 2 wherein the free-space optical communication link further comprises a pump regeneration module disposed at an input to the phase-sensitive amplifier, the pump regeneration module for recovering and regenerating the received pump wave prior to applying the pump wave as an input to the phase-sensitive amplifier.

15. A method of providing free space optical communication comprising the steps of:
    providing an original information signal to be transmitted;
    supplying a pump wave;
    generating an idler signal from a combination of the information signal and the pump wave, the idler signal being a conjugate representation of the information signal;
    transmitting the information signal and the idler signal across a free space optical link to an optical receiver;
    performing phase-sensitive amplification on the received information signal, using the received idler signal and the supplied pump wave; and
    providing the amplified information signal produced by phase-sensitive amplification as an input to an optical receiver.

16. The method as defined in claim 15 wherein the method further comprises the step of:
    transmitting the supplied pump wave with the information signal and the idler signal across the free space link.

17. The method as defined in claim 15 wherein prior to performing the transmitting step, the method includes the step of:
    amplifying the information signal and the idler signal.

18. The method as defined in claim 15, wherein the step of supplying a pump wave further includes the step of controlling a polarization state of the supplied pump wave to maximize parametric gain during the step of generating the idler signal.

19. The method as defined in claim 16 wherein prior to the step of performing phase sensitive amplification, the following steps are performed:
    using a local injection locked laser, regenerating the supplied pump wave to form a regenerated pump wave; and
    using feedback from the output of the phase-sensitive amplification step, providing phase locking between the regenerated pump wave and the received idler and information data signals.

20. The method as defined in claim 19 wherein the method further comprises the step of performing polarization control on the phase-locked, regenerated pump wave prior to providing the pump wave as an input to the phase sensitive amplification step.

21. The method as defined in claim 15 wherein the step of performing phase-sensitive amplification includes performing four-wave mixing of the received information signal and the received idler signal with the supplied pump wave.

* * * * *